(12) United States Patent
Athavle et al.

(10) Patent No.: US 11,357,711 B2
(45) Date of Patent: Jun. 14, 2022

(54) FOAMING CLEANSING COMPOSITION FOR TOPICAL APPLICATION

(71) Applicant: Conopco, Inc., Englewood Cliffs, NJ (US)

(72) Inventors: Varsha Amit Athavle, Mumbai (IN); Mridula Kini, Mumbai (IN); Saumyashree Roy, Kolkata (IN)

(73) Assignee: Conopco, Inc., Englewood Cliffs, NJ (US)

( * ) Notice: Subject to any disclaimer, the term of this patent is extended or adjusted under 35 U.S.C. 154(b) by 269 days.

(21) Appl. No.: 16/316,720

(22) PCT Filed: Jul. 10, 2017

(86) PCT No.: PCT/EP2017/067236
§ 371 (c)(1),
(2) Date: Jan. 10, 2019

(87) PCT Pub. No.: WO2018/011127
PCT Pub. Date: Jan. 18, 2018

(65) Prior Publication Data
US 2019/0224084 A1 Jul. 25, 2019

(30) Foreign Application Priority Data
Jul. 14, 2016 (EP) .................................... 16179393

(51) Int. Cl.
| | | |
|---|---|---|
| *A61K 8/00* | (2006.01) |
| *A61K 8/04* | (2006.01) |
| *A61K 8/25* | (2006.01) |
| *A61K 8/34* | (2006.01) |
| *A61K 8/44* | (2006.01) |
| *A61K 8/46* | (2006.01) |
| *A61K 8/73* | (2006.01) |
| *A61Q 19/10* | (2006.01) |
| *A61K 8/86* | (2006.01) |

(52) U.S. Cl.
CPC ............... *A61K 8/046* (2013.01); *A61K 8/25* (2013.01); *A61K 8/345* (2013.01); *A61K 8/442* (2013.01); *A61K 8/463* (2013.01); *A61K 8/731* (2013.01); *A61K 8/86* (2013.01); *A61Q 19/10* (2013.01); *A61K 2800/48* (2013.01); *A61K 2800/87* (2013.01)

(58) Field of Classification Search
CPC .......... A61K 8/046; A61K 8/25; A61K 8/345; A61K 8/463; A61K 8/731
See application file for complete search history.

(56) References Cited

U.S. PATENT DOCUMENTS

| | | | | |
|---|---|---|---|---|
| 4,666,517 A | * | 5/1987 | Bakar | A61Q 11/00 106/35 |
| 4,795,630 A | * | 1/1989 | Okouchi | A61K 8/02 424/49 |
| 5,447,654 A | | 9/1995 | Millequant et al. | |
| 6,213,166 B1 | * | 4/2001 | Thibiant | A45D 40/16 141/100 |
| 6,242,412 B1 | | 6/2001 | Chambers et al. | |
| 6,641,825 B2 | * | 11/2003 | Scholz | A61K 8/042 424/401 |
| 2002/0010109 A1 | | 1/2002 | Chambers et al. | |
| 2002/0168329 A1 | * | 11/2002 | Kini | A61Q 19/008 424/70.22 |
| 2011/0033555 A1 | | 2/2011 | Kwetkat et al. | |
| 2014/0135245 A1 | * | 5/2014 | Annaheim | A61K 8/0208 510/137 |

FOREIGN PATENT DOCUMENTS

| | | |
|---|---|---|
| EP | 0897719 | 2/1999 |
| GB | 1372663 | 11/1974 |
| GB | 2455404 | 4/2012 |
| WO | WO2006028578 | 3/2006 |
| WO | WO2008132616 | 11/2008 |
| WO | WO2010027721 | 3/2010 |
| WO | WO2012177615 | 12/2012 |

OTHER PUBLICATIONS

Search Report and Written Opinion in PCTEP2017067236; dated Sep. 22, 2017; World Intellectual Property Org. (WIPO).
Dennis Laba; How Do I Thicken My Cosmetic Formula?; Cosmetics and Toiletries; Nov. 30, 2001; pp. 35-44; XP055301132; vol. 116 No. 11.
Search Rerport & Written Opinion in EP16179393; dated Sep. 21, 2016.
IPRP2 in PCT2017067236; dated May 17, 2018.

* cited by examiner

*Primary Examiner* — Necholus Ogden, Jr.
(74) *Attorney, Agent, or Firm* — Stephanie S. DelPonte

(57) ABSTRACT

A cleansing composition for cleansing the skin, comprising by weight of the composition, — 20 to 65 wt. % of one or more polyols; and —5 to 25 wt. % of thickeners, comprising a combination of: a) inorganic thickener selected from silica, chalk, talc, clay and combinations thereof; b) cellulosic thickener selected from cellulose, cellulose ether, cellulose ester and combinations thereof; wherein the weight ratio of the inorganic thickener to the cellulosic thickener is in the range of 4:1 to 40:1; —4 to 12 wt. % of non-soap anionic surfactant; —0 to 8 wt. % of amphoteric surfactant; and wherein the weight ratio of the one or more polyols to the thickeners is in the range of 1:1 to 13:1 and wherein the viscosity of the composition is in the range of 200 to 400 Pa-s, measured at 25° C. after 1 minute at 5 rpm.

18 Claims, No Drawings

FOAMING CLEANSING COMPOSITION FOR TOPICAL APPLICATION

FIELD OF THE INVENTION

The invention relates to a foaming cleansing composition, particularly to a foaming cleansing composition for topical application, that is suitable for cleansing the skin and that comprises synthetic surfactants, polyols and thickeners. The invention further relates to the use of the cleansing composition for the cleansing of the skin and to a container comprising the cleansing composition.

BACKGROUND OF THE INVENTION

Traditionally, soap has been an essential component of personal washing compositions, both in solid and liquid form. However, whilst soap based formulations deliver an abundance of lather (foam), soap is considered to be a harsh anionic surfactant that can damage the stratum corneum, i.e. the outer layer of the skin. Soap is a salt of a fatty acid.

Anionic surfactants, such as soap, are dissociated in water in an amphiphilic anion and a cation, which is in general an alkaline metal (Na+, K+) or a quaternary ammonium. Besides soaps, anionic surfactants include, for instance, alkylbenzene sulphonates, lauryl sulphates, di-alkyl sulfosuccinates and lignosulfonates.

There has been a move to replace soap in washing formulations, at least partially, with synthetic anionic surfactants, such as sodium laureth sulphate. Formulations based on such anionic synthetic surfactants produce an abundance of lather during use, but this lather is perceived as being of poor quality by consumers due to its thinness and lack of creaminess.

Amphoteric surfactants, in particular betaines, are commonly added to these synthetic anionic surfactant formulations as a co-surfactant, to improve the quality. However, this is at the expense of the quantity of lather that is produced during the use of this composition.

Amphoteric or zwitterionic surfactants have two functional groups, one anionic and one cationic. In most cases it is the pH which determines which of the two groups dominates; anionic at alkaline pH and cationic at an acidic pH. Near the isoelectric point, these surfactants display both charges and are truly amphoteric. Amphoteric surfactants, particularly the amino acid ones are quite biocompatible, and are therefore commonly used in pharmaceuticals and cosmetics.

U.S. Pat. No. 6,242,412 B1 describes a liquid personal wash composition comprising a synthetic anionic surfactant and an amphoteric surfactant in a weight ratio in the range of 4:1 to 0.1:1. Incorporation of at least 10% of a polyethylene glycol, having a molecular weight of not more than 100,000, provides both enhanced lather and enhanced mildness.

EP 0,897,719 A1 describes a topical foaming cleansing composition comprising a solid heat generating material that generates heat in contact with water and a substantially anhydrous carrier or diluent, and from 2% to 30% by weight of anionic surfactant.

The market for foaming cleansing compositions is increasing. Consumers prefer foaming cleansing compositions that produce high volumes of stable foam per volume of cleansing composition. Further, there is a need to reduce the amount of packaging that is used by consumers.

SUMMARY OF THE INVENTION

The present inventors have surprisingly found that incorporation of a significant amount of polyols and a combination of two types of thickeners, i.e. inorganic and cellulosic thickeners, in foaming cleansing compositions that are based on an non-soap anionic surfactant and optionally an amphoteric surfactant yields a foaming cleansing composition that generates an exceptionally high amount of lather volume per volume of cleansing composition. This is very advantageous, because consumers need less volume of cleansing composition per wash.

More particularly, the present invention relates to a cleansing composition for cleansing the skin comprising by weight of the composition,
  20 to 65 wt. % of one or more polyols; and
  5 to 25 wt. % of thickeners, comprising a combination of:
    a) inorganic thickener selected from silica, chalk, talc, clay and combinations thereof;
    b) cellulosic thickener selected from cellulose, cellulose ethers, cellulose esters and combinations thereof;
  wherein the weight ratio of the inorganic thickener to the cellulosic thickener is in the range of 4:1 to 40:1;
  4 to 12 wt. % of non-soap anionic surfactant;
  0 to 8 wt. % of amphoteric surfactant; and
  wherein the weight ratio of the one or more polyols to the thickeners is in the range of 1:1 to 13:1 and wherein the viscosity of the composition is in the range of 200 to 400 Pa·s, measured at 25° C. after 1 minute at 5 rpm.

The cleansing composition according to the invention produces a very stable high volume foam with a pleasant creamy texture, amongst others due to small bubbles in the foam. The produced foam is further well-structured and firm.

In addition, the cleansing composition of the present invention offers the advantage that differently coloured volumes of the composition can be introduced together in a container to achieve appealing colour patterns. Unexpectedly, this colour pattern remains intact even when the composition is stored for a prolonged period of time. Colour patterns can suitably be used to generate several visual cues, such as, stripes, ribbons, swirls etc.

The present invention further pertains to the use of the cleansing composition according to the invention for cleansing the skin, preferably cleansing the face.

The present invention further relates to a container comprising two or more differently coloured volumes of the cleansing composition according to the invention.

DETAILED DESCRIPTION OF THE INVENTION

A first aspect of the invention pertains to a cleansing composition comprising by weight of the composition,
  20 to 65 wt. % of one or more polyols; and
  5 to 25 wt. % of thickeners, comprising a combination of:
    a) inorganic thickener selected from silica, chalk, talc, clay and combinations thereof;
    b) cellulosic thickener selected from cellulose, cellulose ethers, cellulose esters and combinations thereof;
  wherein the weight ratio of the inorganic thickener to the cellulosic thickener is in the range of 4:1 to 40:1;
  4 to 12 wt. % of a non-soap anionic surfactant;
  0 to 8 wt. % of amphoteric surfactant; and
    wherein the weight ratio of the one or more polyols to the thickeners is in the range of 1:1 to 13:1 and wherein the viscosity of the composition is in the range of 200 to 400 Pa·s, measured at 25° C. after 1 minute at 5 rpm.

The term "polyols" as used herein refers to alcohols containing multiple hydroxyl groups.

The term "thickener" as used herein refers to a compound which can increase the viscosity of a liquid without substantially changing the other properties of the liquid.

The term "silica" as used herein refers to is a chemical compound that is an oxide of silicon with the chemical formula $SiO_2$.

The term "surfactant" as used herein refers to compounds that lower the surface tension (or interfacial tension) between two liquids or between a liquid and a solid or a gas.

The term "anionic surfactant" as used herein refers to surfactants that contain an anionic functional group(s) at their hydrophilic head. The anionic functional groups are for example sulphates, sulfonates, phosphates, and carboxylates.

The term "non-soap anionic surfactant" as used herein refers to all anionic surfactants except for the salts of a fatty acids.

The term "amphoteric surfactant" as used herein refers to surfactants that have two functional groups, one anionic and one cationic.

The term "viscosity" as used herein refers to the viscosity measured at 25° C. by a Brookfield Viscometer, using spindle RVTD and a Helipath, at 5 rpm for 1 minute in a suitable beaker.

The terms "lathering" and "foaming" as used herein refers to the formation of foam due to the agitation of a soap or a surfactant with water.

The cleansing composition of the present invention has a viscosity in the range of 200 to 400 Pa·s, measured at 25° C. after 1 minute at 5 rpm. More preferably the viscosity of the cleansing composition is in the range of 210 to 390 Pa·s. Most preferably the viscosity of the cleansing composition is within the range of 220 to 380 Pa·s, measured at 25° C. after 1 minute at 5 rpm. The viscosity of the composition can suitably be measured using a Brookfield viscometer and a RVTD spindle and a helipath.

The cleansing composition of the present invention preferably has a pH within the range of 5 to 8. More preferably the pH of the cleansing composition is within the range of 5.5-7.5.

The cleansing composition of the present invention is preferably a foaming cleansing composition.

The cleansing composition of the present invention preferably comprises 30 to 60 wt. % of the one or more polyols. More preferably the cleansing composition comprises 35 to 55 wt. %, most preferably 40 to 50 wt. % of the one or more polyols.

Preferably, the one or more polyols of the cleansing composition are selected from glycerol, sorbitol, polyethylene glycol, propylene glycol and combinations thereof. More preferably, the one or more polyols are selected from glycerol, polyethylene glycol and combinations thereof. Most preferably the cleansing composition comprises a combination of glycerol and polyethylene glycol.

The cleansing composition preferably contains not more than 25 wt. % water. More preferably the water content of the cleansing composition does not exceed 20 wt. %, most preferably the water content does not exceed 15 wt. %.

Preferably, the cleansing composition of the present invention comprises 6 to 22 wt. % of thickeners comprising a combination of:
a) inorganic thickener selected from silica, chalk, talc, clay and combinations thereof;
b) cellulosic thickener selected from cellulose, cellulose ether, cellulose ester and combinations thereof.

More preferably the cleansing composition of the present invention comprises 7 to 20 wt. % of said thickeners, most preferably the composition comprises 8 to 18 wt. % of said thickeners.

In a preferred embodiment, the cleansing composition comprises a combination of the inorganic thickener and the cellulosic thickener, wherein the weight ratio of the inorganic thickener to the cellulosic thickener is in the range 5:1 and 25:1. More preferably the weight ratio of the inorganic thickener to the cellulosic thickener is in the range 10:1 and 20:1

In a preferred embodiment, the cleansing composition of the present invention comprises 2 to 20 wt. % of the inorganic thickener and 0.6 to 3 wt. % of the cellulosic thickener based on the weight of the composition. More preferred is that the cleansing composition of the present invention comprises 4 to 18 wt. % of the inorganic thickener and 0.7 to 2 wt. % of the cellulosic thickener based on the weight of the composition.

Preferably, the inorganic thickener of the cleansing composition is selected from silica, chalk, clay and combinations thereof. More preferably, the inorganic thickener is selected from silica, clay and combinations thereof. Most preferably the inorganic thickener is silica.

Preferably, the silica is selected from precipitated silica, fumed silica and combinations thereof. More preferably the silica is precipitated silica.

Precipitated silica is commonly prepared by precipitation from dilute sodium silicate solutions by the addition of mineral acid and sometimes salt, followed by washing with water and drying.

Preferably the inorganic thickener is contained in the cleansing composition in the form of fine particles.

The mean diameter ($D_{50}$) of the particulate inorganic thickener is preferably between 1 and 35 micron, more preferably the $D_{50}$ is between 5 and 25 micron, most preferably the $D_{50}$ is between 10 and 15 micron. The mean diameter $D_{50}$ can suitably be measured using a Malvern instrument applying laser diffraction.

The BET surface area of the particulate inorganic thickener is preferably at least 100 $m^2/g$, more preferably between 150 and 250 $m^2/g$, most preferably between 170 and 230 $m^2/g$. BET surface area analysis is based on the following: clean solid surfaces adsorb surrounding gas molecules and the Brunauer, Emmett and Teller theory (BET) provides a mathematical model for the process of gas adsorption. This physical adsorption of a gas over the entire exposed surface of a material and the filling of pores is called physisorption and is used to measure total surface area and pore size analysis of nanopores, micropores and mesopores.

Preferably the cellulosic thickener in the cleansing composition is a cellulose ether. More preferably the cellulosic thickener is a cellulose ether selected from methyl cellulose, ethyl cellulose, hydroxyethylmethyl cellulose, hydroxypropyl cellulose and carboxymethyl cellulose. Even more preferably the cellulosic thickener is a cellulose ether selected from hydroxyethylmethyl cellulose, hydroxypropyl cellulose and carboxymethyl cellulose. Most preferably the cellulosic thickener is carboxymethyl cellulose.

Preferably, the weight ratio of the one or more polyols to the thickeners in the cleansing composition is in the range of 1.5:1 to 11:1. More preferably, the weight ratio of the one or more polyols to the thickeners in the cleansing composition is in the range of 2:1 to 9:1.

The cleansing composition of the present invention preferably comprises 5 to 10 wt. % of the non-soap anionic surfactant. More preferably the cleansing composition comprises 6 to 9 wt. % of the non-soap anionic surfactant and most preferably the cleansing composition comprises 6.5 to 8.5 wt. % of the non-soap anionic surfactant.

The non-soap anionic surfactant of the cleansing composition of the present invention is preferably selected from alcohol sulphate, alcohol sulfonate, alcohol phosphate, alcohol phosphonate, alkyl sulphate, alkyl sulfonate, alkylaryl sulphate, alkylaryl sulfonate, alkali metal salt of fatty acid, ammonium salt of fatty acid, sulfonated amine, sulfonated amide, fatty sarcosinate, linear alkylated sulfonate, alcohol ether sulphate, secondary alkane sulfonate and combinations thereof.

More preferably the non-soap anionic surfactant is selected from sodium trideceth sulphate, sodium laureth sulphate, ammonium laureth sulphate and combinations thereof.

Even more preferably the non-soap anionic surfactant is selected from sodium laureth sulphate, ammonium laureth sulphate and combinations thereof. Most preferably the non-soap anionic surfactant is sodium laureth sulphate.

It is preferred that the cleansing composition does not comprise sodium lauryl sulphate, as this surfactant can be harsh for the skin.

The cleansing composition of the present invention preferably comprises 1 to 6 wt. % of amphoteric surfactant. More preferably the cleansing composition comprises 2 to 5 wt. % of amphoteric surfactant. Most preferably the cleansing composition comprises 3 to 4.5 wt. % of amphoteric surfactant.

The amphoteric surfactant of the cleansing composition is preferably selected from amino acid based surfactants, betaines, sultaines, alkyl amphocarboxylates and combinations thereof. More preferably, the amphoteric surfactant is selected from amino acid based surfactants, betaines and combinations thereof. Even more preferably the amphoteric surfactant is selected from betaines. The most preferred amphoteric surfactant is cocoamidopropyl betaine.

In a preferred embodiment of the present invention, the cleansing composition comprises further components selected from water, fragrance, colouring agent, vitamins, scrubbing agents, pH adjusters and combinations thereof.

A second aspect of the invention relates to the use of the cleansing composition, as described herein before, for cleansing the skin, wherein said use comprises applying the cleansing composition on the skin and spreading it as to create lathering of the cleansing composition on the skin.

A more preferred use of the cleansing composition comprises applying the cleansing composition on the skin in combination with water and spreading it as to create lathering of the cleansing composition on the skin.

The use of the cleaning composition is particularly suited for the cleansing of the face.

A third aspect of the invention relates to a container comprising two or more differently coloured volumes of the cleansing composition as described herein before.

A preferred container according to the present invention is a container, wherein the two or more differently coloured volumes of cleansing composition in the container are in direct contact with each other.

The invention is further illustrated by the following non-limiting examples.

EXAMPLES

Example 1

A foaming cleansing composition according to the present invention (composition 1) was compared with a commercially available high foaming cleansing composition under the name "Purifying Neem Face Wash", (cleansing composition A).

Cleansing composition 1 was prepared on the basis of the recipe shown in Table 1.

TABLE 1

| Ingredients | w/w % |
| --- | --- |
| Glycerine | 42.6 |
| PEG 1500 | 2 |
| Sodium laureth sulphate (SLES 28%) | 28 |
| Cocoamido propyl betaine (CAPB 30%) | 12 |
| 10% NaOH | 0.3 |
| Precipitated Silica (Mfil)[1] | 13 |
| Sodium carboxy methyl cellulose (SCMC 9H) | 0.85 |
| Minors | 1.25 |

[1]The precipitated silica has a mean diameter ($D_{50}$) of 10.0-15.0 μm measured by Malvern using laser diffraction and a BET surface area of around 190 $m^2/g$.

Composition 1 was prepared as follows:

Glycerine, precipitated silica and sodium carboxy methyl cellulose were mixed In a Stephan mixer until the precipitated silica was completely wetted to obtain a first mixture.

Subsequently 28% SLES and 30% CAPB were added to the first mixture and this mixture was mixed for 10-15 minutes under vacuum in order to avoid aeration and to obtain a second mixture.

Melted PEG 1500 was added to the second mixture and this mixture was mixed for 5 minutes under vacuum to obtain a third mixture.

To finish, 10% NaOH solution was added to the third mixture to bring the pH between 5.5 and 7.5, and minors such as preservatives, perfume, and colouring agents were added to obtain the final mixture. The final mixture was mixed under vacuum until the final mixture was completely deaerated.

Lather Test Method i. 0.5 gram of a cleansing composition sample was weighed in a beaker;

ii. Gently 99.5 ml lukewarm water was poured in the beaker, followed by gently stirring at a temperature between 40-45 C until the cleansing composition sample was completely dissolved;

iii. Subsequently the solution was allowed to cool down to room temperature (25-27° C.);

iv. 30 ml of this solution was transferred into a 300 ml measuring cylinder;

v. This cylinder was vigorously shaken 20 times to cover an arc of length of 46 cm (18 inches) and with central angle of 90°;

vi. Directly thereafter the volume of lather was measured.

Results of the Lather Test

The results of the lather test are presented in table 2.

TABLE 2

| | Volume (ml) of lather generated |
| --- | --- |
| Example 1 | 250 ml |
| Example A | 100 ml |

Example 2

The viscosity of two cleansing compositions was compared. The cleansing compositions were prepared using the ingredients as indicated in table 3 and by applying the method of preparing as described above in example 1.

TABLE 3

| Ingredients | 2 (w/w %) | B (w/w %) |
|---|---|---|
| Glycerine | 42.6 | 42.6 |
| PEG 1500 | 2 | 2 |
| Sodium laureth sulphate (SLES 28%) | 28 | 28 |
| Cocoamido propyl betaine (CAPB 30%) | 12 | 12 |
| 10% NaOH | 0.3 | 0.3 |
| Precipitated Silica (Mfil)[1] | 13 | 3 |
| Sodium carboxy methyl cellulose | 0.85 | 0.85 |
| Water | — | 10 |
| Minors | 1.25 | 1.25 |

[1]The precipitated silica has a mean diameter ($D_{50}$) of 10.0-15.0 µm measured by Malvern using laser diffraction and a BET surface area of around 190 m$^2$/g.

Viscosity Test

The viscosity was measured using a Brookfield viscometer. The following method was applied to measure the viscosity of the samples.
1. Place the sample in a suitable container beneath the Brookfield viscometer head and control the temperature of the sample to 25° C.;
2. Elevate the sample until the surface of the sample is almost in contact with the spindle RVTD;
3. Start the viscometer and switch on the helipath;
4. As soon as the spindle, turning at 5 rpm, contacts the surface of the sample, start the stopwatch;
5. After one minute take the viscometer reading and record the result;
6. Stop the viscometer and the helipath, remove the sample.

Results

The viscosity measurement results are presented in Table 4. Cleansing composition B had a significant lower viscosity compared to cleansing composition 2. It was further observed that cleansing composition 2 produced a lather which exhibited creamy properties and long lasting stability, whereas Cleansing composition B produced unstable foam with large air bubbles.

TABLE 4

| | Thickener (wt. %) | Viscosity (Pa · s) |
|---|---|---|
| 2 | 13.85 | 338 |
| B | 3.85 | 80 |

Note: Composition B is outside the invention

Example 3

The lather produced by two cleansing compositions was compared. The cleansing compositions were prepared using the ingredients as indicated in Table 5 and by applying the method of preparation as described above in example 1.

TABLE 5

| Ingredients | 3 (w/w %) | C (w/w %) |
|---|---|---|
| Glycerine | 42.6 | 42.6 |
| PEG 1500 | 2 | 2 |
| Sodium laureth sulphate (SLES 28%) | 28 | 8 |
| Cocoamido propyl betaine (CAPB 30%) | 12 | 5 |
| 10% NaOH | 0.3 | 0.3 |

TABLE 5-continued

| Ingredients | 3 (w/w %) | C (w/w %) |
|---|---|---|
| Precipitated Silica (Mfil)[1] | 13 | 13 |
| Sodium carboxy methyl cellulose | 0.85 | 0.85 |
| Water | — | 27 |
| Minors | 1.25 | 1.25 |

[1]The precipitated silica has a mean diameter ($D_{50}$) of 10.0-15.0 µm measured by Malvern using laser diffraction and a BET surface area of around 190 m$^2$/g.

Method of Producing Foam
i. 0.5 gram of a cleansing composition sample was weighed in a beaker;
ii. Gently 99.5 ml lukewarm water was poured in the beaker, followed by gently stirring at a temperature between 40-45 C until the cleansing composition sample was completely dissolved;
iii. Subsequently the solution was allowed to cool down to room temperature (25-27° C.);
iv. 30 ml of this solution was transferred into a 300 ml measuring cylinder;
v. This cylinder was vigorously shaken 20 times to cover an arc of length of 46 cm (18 inches) and with central angle of 90°;
vi. After the shaking the quality of the foam was assessed.

Results

Cleansing composition 3 generated a large volume of creamy stable foam with small bubbles. The foam of cleansing composition 3 was similar to the foam produced by a facewash comprising soap as anionic surfactant. Whereas cleansing composition C produced a small volume of transparent foam, with large bubbles, which subsided over time. The type of foam of cleansing composition C is typical for cleansing compositions comprising synthetic surfactants.

Example 4

The storage stability of the Cleansing composition 1, as described herein before in example 1, was assessed. Cleansing composition 1 comprised two volumes that were in contact with each other. One volume was red colored and the other volume was pearl colored.

An accelerated storage stability test was conducted by exposing cleansing composition 1 to different temperatures for a total period of 12 weeks. The specific conditions are indicated in Table 6. The parameters that were evaluated at different time points were appearance, odour, colour, retention of integrity, viscosity and pH.

TABLE 6

| Storage temperature (° C.) | Evaluation time points (week) |
|---|---|
| 4 | 0, 4, 8, 12 |
| 25 | 0, 4, 8, 12 |
| 45 | 0, 4, 8, 12 |
| 50 | 0, 4 |

It was observed that all evaluated parameters remained stable during the accelerated storage stability test. The two volumes of cleansing composition 1 with different colors remained separated from each other. The appearance, odour, color and retention of integrity remained the same, even at the higher temperatures.

In table 7 below the results for the viscosity measurements and the pH measurements at different time points for the different temperatures are indicated.

TABLE 7

| Time point (wk) | Viscosity (Pa·s) | | | | pH | | | |
|---|---|---|---|---|---|---|---|---|
| | 4° C. | 25° C. | 45° C. | 50° C. | 4° C. | 25° C. | 45° C. | 50° C. |
| 0 | 328 | 328 | 328 | 328 | 6.78 | 6.78 | 6.78 | 6.78 |
| 4 | 339 | 338 | 337 | 340 | 6.75 | 6.77 | 6.76 | 6.77 |
| 8 | 339 | 337 | 337 | — | 6.76 | 6.76 | 6.75 | — |
| 12 | 339 | 338 | 337 | — | 6.76 | 6.77 | 6.76 | — |

The invention claimed is:

1. A container comprising at least two cleansing compositions, wherein each cleansing composition comprises:
    40 to 60 wt. % of one or more polyols selected from glycerol, polyethylene glycol and combinations thereof; and
    6 to 22 wt. % of thickeners, comprising a combination of:
       inorganic thickener selected from silica, chalk, talc, clay and combinations thereof;
       cellulosic thickener selected from cellulose, cellulose ether, cellulose ester and combinations thereof;
       wherein the weight ratio of the inorganic thickener to the cellulosic thickener is in the range of 4:1 to 40:1;
    4 to 12 wt. % of non-soap anionic surfactant; and
    1 to 6 wt. % of amphoteric surfactant; and
    wherein the weight ratio of the one or more polyols to the thickeners is in the range of 1:1 to 13:1 and wherein the viscosity of the composition is in the range of 200 to 400 Pa·s, measured at 25° C. after 1 minute at 5 rpm;
    wherein each cleansing composition contains the same amount of each of the at least one or more polyols, thickeners, the non-soap anionic surfactant and the amphoteric surfactant; and
    wherein each cleansing composition is a different color.

2. The container according to claim 1, wherein the one or more polyols are a combination of glycerol and polyethylene glycol.

3. The container according to claim 1, wherein the inorganic thickener is silica.

4. The container according to claim 3, wherein the inorganic thickener is contained in the cleansing composition in the form of fine particles.

5. The container according to claim 1, wherein the cellulosic thickener is a cellulose ether.

6. The container according to claim 5, wherein the cellulose ether is carboxymethyl cellulose.

7. The container according to claim 1, wherein the weight ratio of the inorganic thickener to the cellulosic thickener is in the range 5:1 and 25:1.

8. The container according to claim 1, wherein each cleansing composition comprises 2 to 20 wt. % of the inorganic thickener and 0.6 to 3 wt. % of the cellulosic thickener based on the weight of the composition.

9. The container according to claim 1, wherein the anionic surfactant is selected from alcohol sulfate, alcohol sulfonate, alcohol phosphate, alcohol phosphonate, alkyl sulfate, alkyl sulfonate, alkylaryl sulfate, alkylaryl sulfonate, sulfonated amine, sulfonated amide, fatty sarcosinate, linear alkylated sulfonate, alcohol ether sulfate, secondary alkane sulfonate and combinations thereof.

10. The container according to claim 1, wherein the amphoteric surfactant is selected from amino acid surfactants, betaines, sultaines, alkyl amphocarboxylates and combinations thereof.

11. The container according to claim 10, wherein the amphoteric surfactant is cocoamidopropyl betaine.

12. The container according to claim 1 wherein the at least two cleansing compositions in the container are in direct contact with each other.

13. The container according to claim 3, wherein the silica is precipitated silica.

14. The container according to claim 1, wherein each cleansing composition remains stable for at least 4 weeks at a temperature of 50° C. or less.

15. The container according to claim 1, wherein each cleansing composition maintains the same appearance, color and odor for at least 4 weeks.

16. The container according to claim 1, wherein each cleansing composition maintains the same appearance, color and odor for at least 8 weeks.

17. The container according to claim 1, wherein each cleansing composition maintains the same appearance, color and odor for at least 12 weeks.

18. A container comprising at least two cleansing compositions, wherein each cleansing composition comprises:
    40 to 50 wt. % of one or more polyols selected from glycerol, polyethylene glycol and combinations thereof; and
    8 to 18 wt. % of thickeners, comprising a combination of:
       inorganic thickener selected from silica, chalk, talc, clay and combinations thereof;
       cellulosic thickener wherein the cellulose thickener is carboxymethyl cellulose;
       wherein the weight ratio of the inorganic thickener to the cellulosic thickener is in the range of 10:1 to 20:1;
    6.5 to 8.5 wt. % of non-soap anionic surfactant; and
    3 to 4.5 wt. % of amphoteric surfactant; and
    wherein the weight ratio of the one or more polyols to the thickeners is in the range of 2:1 to 9:1 and wherein the viscosity of the composition is in the range of 200 to 400 Pa·s, measured at 25° C. after 1 minute at 5 rpm;
    wherein each cleansing composition contains the same amount of each of the at least one or more polyols, thickeners, the non-soap anionic surfactant and the amphoteric surfactant;
    wherein each cleansing composition is a different color; and
    wherein each cleansing composition maintains same appearance, color and odor for at least 4 weeks.

* * * * *